United States Patent
Ahn et al.

(10) Patent No.: US 10,533,209 B2
(45) Date of Patent: Jan. 14, 2020

(54) IMMOBILIZED ENZYMATIC REACTOR

(71) Applicant: Waters Technologies Corporation, Milford, MA (US)

(72) Inventors: Joomi Ahn, Johnston, RI (US); Moon Chul Jung, Cambridge, MA (US); Kevin D. Wyndham, Upton, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 15/884,902

(22) Filed: Jan. 31, 2018

(65) Prior Publication Data

US 2018/0171379 A1  Jun. 21, 2018

Related U.S. Application Data

(62) Division of application No. 13/985,900, filed as application No. PCT/US2012/024869 on Feb. 13, 2012, now Pat. No. 9,890,411.

(60) Provisional application No. 61/474,155, filed on Apr. 11, 2011, provisional application No. 61/443,380, filed on Feb. 16, 2011.

(51) Int. Cl.
| | |
|---|---|
| *C12Q 1/37* | (2006.01) |
| *C12N 11/06* | (2006.01) |
| *C12N 11/14* | (2006.01) |
| *C12M 1/40* | (2006.01) |
| *C12M 1/34* | (2006.01) |
| *C12Q 1/48* | (2006.01) |

(52) U.S. Cl.
CPC .............. *C12Q 1/37* (2013.01); *C12M 21/18* (2013.01); *C12M 41/40* (2013.01); *C12N 11/06* (2013.01); *C12N 11/14* (2013.01); *C12Q 1/48* (2013.01)

(58) Field of Classification Search
None
See application file for complete search history.

(56) References Cited

U.S. PATENT DOCUMENTS

| | | |
|---|---|---|
| 4,894,468 A | 1/1990 | Wilchek et al. |
| 4,994,373 A | 2/1991 | Stavrianopoulos et al. |
| 6,686,035 B2 | 2/2004 | Jiang et al. |
| 7,064,197 B1 | 6/2006 | Rabbani et al. |
| 7,201,844 B1 | 4/2007 | Hammen et al. |
| 2005/0095690 A1 | 5/2005 | Naik et al. |
| 2008/0241877 A1 | 10/2008 | Ying et al. |
| 2009/0203068 A1 | 8/2009 | Lopez-Ferrer |
| 2009/0256068 A1 | 10/2009 | Petritis et al. |
| 2011/0195430 A1 | 8/2011 | Lopez-Ferrer |
| 2012/0003689 A1 | 1/2012 | Ying et al. |
| 2012/0100565 A1 | 4/2012 | Lopez-Ferrer |

FOREIGN PATENT DOCUMENTS

| | | |
|---|---|---|
| JP | H04269656 A | 9/1992 |
| JP | 2003177129 A | 6/2003 |
| JP | 2008532514 A | 8/2008 |
| JP | 2011027429 A | 2/2011 |
| WO | 2009/099685 A2 | 8/2009 |
| WO | 2011/014372 A1 | 2/2011 |

OTHER PUBLICATIONS

Rezaei, K., and F. Temelli. "On-line extraction-reaction of canola oil using immobilized lipase in supercritical CO2." The Journal of Supercritical Fluids 19.3 (2001): 263-274. (Year: 2001).*
Girelli et al. "Application of immobilized enzyme reactor in on-line high performance liquid chromatography: A review." J. Chromat. B. 819.1(2005): 3-16.
Lee et al. "Rapid and efficient protein digestion using trypsin-coated magnetic nanoparticles under pressure cycles." Proteomics. 11(2011):309-318.
Peper et al. "Immobilitization and characterization of benzoylformate decarboxylast from Pseudomonas putida on spherical silica carrier." Bioprocess Biosyst. Eng. 34(2011):671-680.
Van Roon et al. "Biocatalysts: Measurement, modelling and design of heterogeneity." Biotechnol. Advances. 25(2007):137-147.
Abdullah, A.Z., N.S. Sulaiman, and A.H. Kamaruddin. "Biocatalytic esterification of citronellol with lauric acid by immobilized lipase on aminopropyl-grafted mesoporous SBA-15." Biochemical Engineering Journal 44.2 (2009): 263-270.
Exhibit A: Waters Corporation, "A Review of Waters Hybrid Particle Technology. Part 2. Ethylene-Bridged [BEH Technology] Hybrids and Their Use in Liquid Chromatography", 8 pages, 2004.
Gao, Siliang, et al. "Effect of pore diameter and cross-linking method on the immobilization efficiency of Candida rugosa lipase in SBA-15." Bioresource Technology 101.11 (2010): 3830-3837.
Han, Yu, Su Seong Lee, and Jackie Y. Ying. "Pressure-driven enzyme entrapment in siliceous mesocellular foam." Chemistry of Materials 18.3 (2006): 643-649.
Instruments News (2012), 4(5):1-21.
Jackson, Michael A., Isa K. Mbaraka, and Brent H. Shanks. "Esterification of oleic acid in supercritical carbon dioxide catalyzed by functionalized mesoporous silica and an immobilized lipase." Applied Catalysis A: General 310 (2006): 48-53.

(Continued)

*Primary Examiner* — Robert J Yamasaki
(74) *Attorney, Agent, or Firm* — Womble Bond Dickinson (US) LLP; Deborah M. Vernon

(57) ABSTRACT

An immobilized enzymatic reactor can include a wall defining a chamber having an inlet and an outlet; a solid stationary phase covalently linked to an enzyme and disposed within the chamber; and a pressure modulator in fluid communication with the chamber and adapted to support continuous flow of a liquid sample comprising a polymer analyte through the inlet, over the solid stationary phase, and out of the outlet under a pressure between about 2,500 and 35,000 psi. In one example, the solid stationary phase includes inorganic/organic hybrid particles in an ultra performance liquid chromatography system, the enzyme is a protease, and the polymer analyte is a polypeptide. The immobilized enzymatic reactor can prepare an analyte for applications such as for hydrogen deuterium exchange mass spectrometry.

12 Claims, 5 Drawing Sheets

(56) References Cited

OTHER PUBLICATIONS

Jones, Lisa M., et al. "Online, high-pressure digestion system for protein characterization by hydrogen/deuterium exchange and mass spectrometry." Analytical Chemistry 82.4 (2010): 1171-1174.

Ma, Junfeng, et al. "Recent advances in immobilized enzymatic reactors and their applications in proteome analysis." Analytica Chimica Acta 632.1 (2009): 1-8.

Ma et al., "Organic-Inorganic Hybrid Silica Monolith Based Immobilized Trypsin Reactor with High Enzymatic Activity", Analytical Chemistry, (2008), 80(8):2949-2956.

Maes et al., "Characterization of an immobilized hexose oxidase reactor for mono- and oligosaccharide determination by liquid chromatography", 1993, Analytica Chimica Acta, vol. 284, No. 2, pp. 281-290.

Mellors, et al., "Use of 1.5-microm porous ethyl-bridged hybrid particles as a stationary-phase support for reversed-phase ultrahigh-pressure liquid chromatography." Anal Chem. 76(18):5441-50 (2004).

Na, Wei, et al. "Effective immobilization of enzyme in glycidoxypropyl-functionalized periodic mesoporous organosilicas (PMOs)." Microporous and Mesoporous Materials 134.1 (2010): 72-78.

Rezaei, Karamatollah, F. Temelli, and E. Jenab. "Effects of pressure and temperature on enzymatic reactions in supercritical fluids." Biotechnology Advances 25.3 (2007): 272-280.

Schoenherr et al., "CE-Microreactor-CE-MS/MS for Protein Analysis", Analytical Chemistry, (2007), 79(6): 2230-2238.

Supplementary European Search Report for EP 12 74 7041; dated Jul. 8, 2014.

Wales, T. et al., "High-Speed and High-Resolution UPLC Separation at Zero Degrees Celsius", Analytical Chemistry, vol. 80, No. 17, pp. 6815-6820, 2008.

\* cited by examiner

IMMOBILIZED ENZYMATIC REACTOR

RELATED APPLICATIONS

This application claims the benefit of and priority to U.S. patent application Ser. No. 13/985,900 filed Nov. 21, 2013, which is a National Stage Application of international application no. PCT/US2012/024869, filed Feb. 13, 2012, which claims priority to U.S. provisional patent application No. 61/443,380 filed Feb. 16, 2011, and U.S. provisional patent application No. 61/474,155, filed Apr. 11, 2011, each of which are owned by the assignee of the instant applications. Each of the foregoing applications is incorporated herein by reference in its entirety.

FIELD OF THE TECHNOLOGY

The technology relates generally to immobilized enzymatic reactors (IMERs). The technology relates more particularly to high-pressure, continuous flow systems using a solid stationary phase covalently linked to an enzyme in the analysis of liquid samples comprising a polymer analyte.

BACKGROUND OF THE TECHNOLOGY

An immobilized enzyme is an enzyme that is attached to an insoluble material, which allows enzymes to be held in place throughout a reaction, separated from the products after the reaction, and used again if desired. There are three general methods for immobilizing an enzyme in an IMER. The first general method includes adsorption on glass, alginate beads or matrix, in which the enzyme is attached to the outside of an inert material. As adsorption is not a chemical reaction, the active site of the immobilized enzyme may be blocked by the matrix or bead, reducing the activity of the enzyme. The second general method includes entrapment, in which the enzyme is trapped in insoluble beads or microspheres, such as calcium alginate beads. However, the insoluble substance can hinder the arrival of reactants and the exit of products. The third general method is cross-linkage, in which the enzyme is covalently bonded to a matrix through a chemical reaction.

Covalently-linked IMERs and IMER media are available in various forms. For example, POROSZYME media, available from APPLIED BIOSYSTEMS (California, USA), employ polystyrenedivinylbenzene particles. STYROSZYME™ media, available from OraChrom, Inc. (Massachusetts, USA), employs fully pervious poly(styrene-divinylbenzene) matrices. Agarose bead media is also available from Thermo Fisher Scientific Inc (Massachusetts, USA). Presently, most commercial IMERs use these media under low pressure conditions.

BRIEF SUMMARY OF THE TECHNOLOGY

The technology, in various embodiments, relates to apparatuses, methods, and kits for high-pressure, online/continuous flow IMER systems using a solid stationary phase covalently linked to an enzyme in the analysis of liquid samples comprising a polymer analyte. The solid stationary phase and system are adapted for high-pressure, continuous-flow operation, which can increase the efficiency and ease of use for the apparatuses, methods, and kits. In one example, the chamber can be an ultra performance liquid chromatography (UPLC) column, the solid stationary phase can be inorganic/organic hybrid particles (e.g., ethylene-bridged (BEH) particles), the enzyme can be a protease, the polymer analyte can be a protein, and the system can support continuous flow of a liquid sample comprising the protein under a pressure between about 2,500 and 15,000 psi. Thus, the apparatuses can prepare an analyte for applications in proteomics such as for hydrogen deuterium exchange mass spectrometry (HDX MS). Other examples and applications will be understood by persons of ordinary skill in the art from the disclosure and claims.

In one aspect, the technology features an apparatus that includes a wall defining a chamber having an inlet and an outlet, and a solid stationary phase covalently linked to an enzyme and disposed within the chamber. The apparatus also includes a pressure modulator in fluid communication with the chamber and adapted to support continuous flow of a liquid sample comprising a polymer analyte through the inlet, over the solid stationary phase, and out of the outlet under a pressure between about 2,500 and 35,000 psi.

In another aspect, the technology features a method that includes continuously flowing a liquid sample comprising a polymer analyte over a solid stationary phase covalently linked to an enzyme, under a pressure between about 2,500 and 35,000 psi, thereby enzymatically cleaving the polymer analyte.

In still another aspect, the technology features a method that includes selecting a solid stationary phase that can be linked to an enzyme and operate under a pressure between about 2,500 and 35,000 psi. The method also includes disposing the solid stationary phase, covalently linked to an enzyme, within a chamber having an inlet and an outlet. The chamber is in fluid communication with a pressure modulator adapted to support continuous flow of a liquid sample comprising a polymer analyte through the inlet, over the solid stationary phase, and out of the outlet under the pressure.

In various embodiments, the solid stationary phase can include inorganic/organic hybrid particles. The solid stationary phase can include ethylene-bridged (BEH) particles.

In some embodiments, the solid stationary phase can include a monolith, porous material, superficially porous material, porous particles, or superficially porous particles. The solid stationary phase can include pores having a mean pore volume within the range of 0.1-2.5 cm$^3$/g. The solid stationary phase can include pores having a mean pore diameter within the range of 100-1000 Angstroms. The solid stationary phase can be nonporous. The solid stationary phase can include ceramic, silica, inorganic silica, surface hybrid, or metal oxide. The solid stationary phase can include particles having a mean size within the range of 0.1-10 microns.

In certain embodiments, the covalent linker can include an organofunctionalized silane linker. The covalent linker can be triethoxysilylbutyraldehyde.

In various embodiments, the pressure used in the apparatus or in one or more of the methods is within the range of 8,000-15,000 psi.

In some embodiments, the apparatus can include one or more of the following: a trapping column configured to collect the analyte flowing out of the outlet; a chromatography column configured to separate the collected analyte; and a mass spectrometer configured to analyze the separated analyte.

In certain embodiments, one or more of the methods can include one or more of the following: collecting analyte flowing out of the outlet; separating the collected analyte by liquid chromatography; and analyzing the separated analyte by mass spectrometry.

In various embodiments, one or more of the methods includes cycling the pressure between (i) the pressure between about 2,500 and 35,000 psi and (ii) a second pressure below about 2,500, while continuously flowing the liquid sample.

In some embodiments, the solid stationary phase is also linked to a capture group. The capture group can be a high affinity/specific capture agent (e.g., an antibody or antibody conjugate) or a low affinity/nonspecific capture agent. The capture group can be covalently linked to the solid stationary phase.

Online, high-pressure methods according to the technology have advantages including simpler operation and sample preparation than conventional methods, as well as increased throughput. Such online, high pressure methods also have advantages including improved protein digestions efficiency and the ability to digest polymers that are resistant to digestion at lower pressures. A polymer analyte can be a biopolymer such as a proteins, polypeptide, carbohydrate, deoxyribonucleic acid, or ribonucleic acid. A polymer analyte can be a non-natural polymer (hetero or homopolymer) having a linkage that can be cleaved by an enzyme.

Other aspects and advantages of the technology will become apparent from the following drawings and description, all of which illustrate principles of the technology, by way of example only.

BRIEF DESCRIPTION OF THE SEVERAL VIEWS OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

DETAILED DESCRIPTION OF THE TECHNOLOGY

Figure 1:
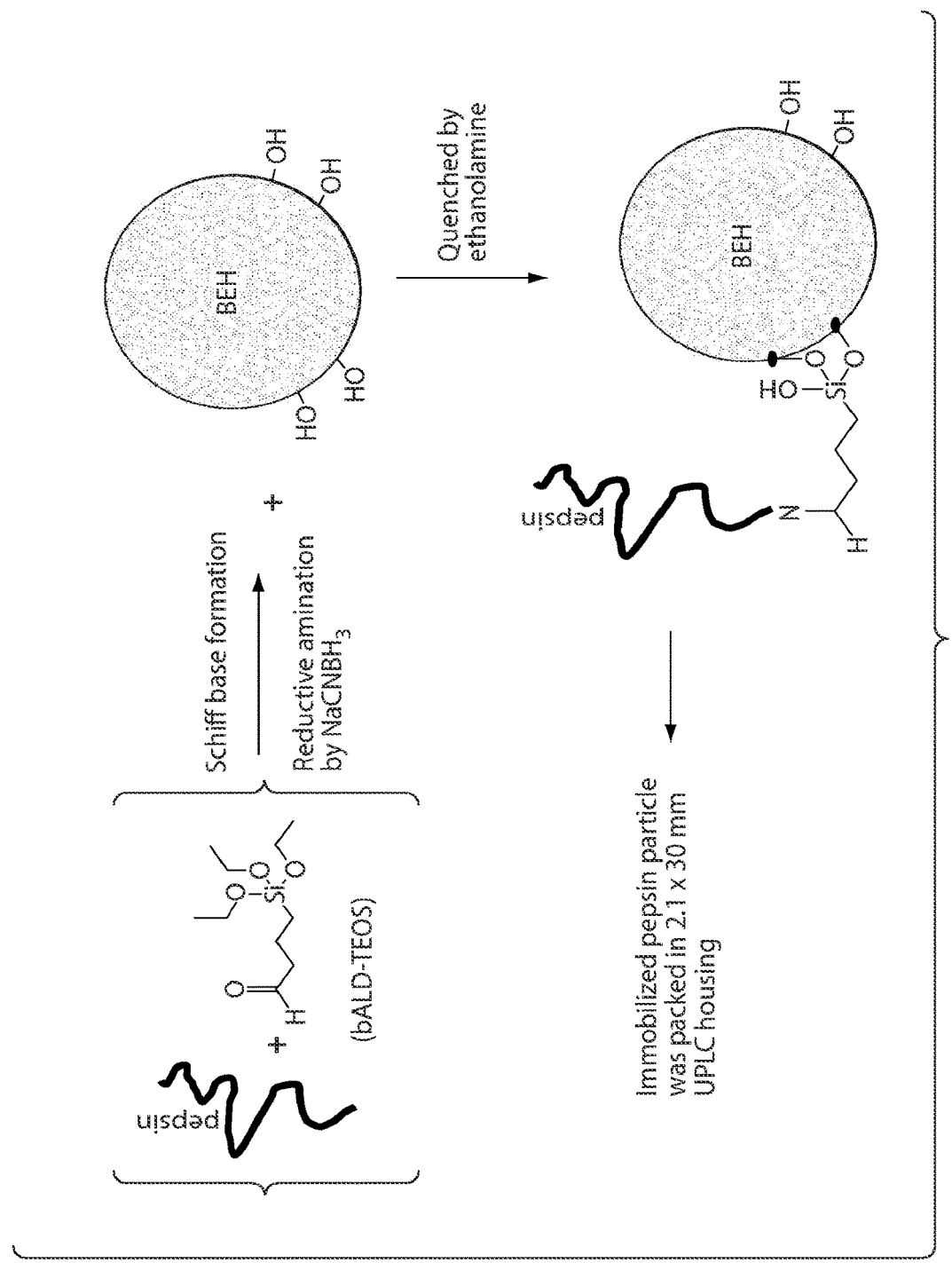
FIG. 1 shows an example solid stationary phase preparation.

The technology includes apparatuses, methods, and kits for high-pressure, continuous flow (e.g., online) IMER systems using a solid stationary phase covalently linked to an enzyme in the analysis of liquid samples comprising a polymer analyte. Such online methods have advantages including simpler operation and sample preparation than conventional methods. Such high pressure methods also have advantages including improved protein digestions efficiency and the ability to digest polymers that are resistant to digestion at lower pressures. A polymer analyte can be a biopolymer such as a proteins, polypeptide, carbohydrate, deoxyribonucleic acid, or ribonucleic acid. A polymer analyte can be a non-natural polymer (hetero or homopolymer) having a linkage that can be cleaved by an enzyme.

IMERs have numerous applications, for example in proteomics and biotechnology. One common application for IMER systems is proteolysis, which is an important sample preparation step in protein characterization (e.g., prior to analysis, for example, by LC-MS). Protein digestion is generally performed offline by contacting a protease and a sample protein, to cleave the sample protein into smaller fractionated peptides. Offline protein digestion is a standard protocol, but can have undesirable complications such as modification and reduction of the polypeptides. Other disadvantages of offline digestion include higher operator time and higher enzyme use (e.g., higher cost), when compared to methods according to the technology. Although protein digestion is provided as an illustrative example, the technology can be applied to essentially any analyte preparation or analysis that employs an enzymatic process.

Protein digestion can also be performed in an IMER. Commercially available IMER media include 20 µm POROSZYME media (polystyrenedivinylbenzene particles), available from APPLIED BIOSYSTEMS California, USA, STYROSZYME™ media (fully pervious poly(styrene-divinylbenzene) matrices, available from OraChrom, Inc., Massachusetts, USA), and agarose bead media. However, these media can only be used at relatively low pressure (e.g., below 2,000 psi) because higher pressures will destroy the media and render the IMER inoperative. Therefore, such media are fundamentally limited in their applications and operating conditions.

In contrast to the prior art, the technology employs a solid stationary phase adapted for online operation under high pressure. High pressure can include a pressure between about 2,500 and 35,000 psi, for example, a pressure within the range of 8,000-15,000 psi. One example of a pressure-resistant solid support is BEH particles. Modification on the solid support can be achieved with a linker, e.g., an organofunctional silane chemical linker such as triethoxysilyl-butyraldehyde, which can then be used to immobilize a protease. This solid stationary phase can be packed in a column to produce an IMER, which can then be used to digest proteins in an on-line LC system. On-line digestion can be performed under high pressure, for example, in a Waters Corporation (Massachusetts, USA) UPLC-MS system for hydrogen deuterium exchange mass spectrometry (HDX MS).

Importantly, solid stationary phase or support is not destroyed or rendered non-functional under high pressure operation. The technology also supports on-line operation (e.g., operation under pressure while continuously flowing a sample over the solid support, as opposed to off-line methods such as separate sample preparation or static pressurized columns with sample cycling). On-line operation can increase efficiency by allowing the fractionated peptides to be collected in a trapping column and then separated by a chromatograph in a rapid and continuous manner. Likewise, high pressure operation can also increase efficiency, for example, by increasing the efficiency of proteolytic digestions, improving analytical measurements, and increasing the rate of the operation of the device.

Definitions

As used above, the term "aliphatic group" includes organic compounds characterized by straight or branched chains, typically having between 1 and 22 carbon atoms.

Aliphatic groups include alkyl groups, alkenyl groups and alkynyl groups. In complex structures, the chains can be branched or cross-linked. Alkyl groups include saturated hydrocarbons having one or more carbon atoms, including straight-chain alkyl groups and branched-chain alkyl groups. Such hydrocarbon moieties may be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl and the like. As used herein, the term "nitro" means —$NO_2$; the term "halogen" designates —F, —Cl, —Br or —I; the term "thiol" means SH; and the term "hydroxyl" means —OH. Thus, the term "alkylamino" as used herein means an alkyl group, as defined above, having an amino group attached thereto. Suitable alkylamino groups include groups having 1 to about 12 carbon atoms, or from 1 to about 6 carbon atoms. The term "alkylthio" refers to an alkyl group, as defined above, having a sulfhydryl group attached thereto. Suitable alkylthio groups include groups having 1 to about 12 carbon atoms, or from 1 to about 6 carbon atoms. The term "alkylcarboxyl" as used herein means an alkyl group, as defined above, having a carboxyl group attached thereto. The term "alkoxy" as used herein means an alkyl group, as defined above, having an oxygen atom attached thereto. Representative alkoxy groups include groups having 1 to about 12 carbon atoms, or 1 to about 6 carbon atoms, e.g., methoxy, ethoxy, propoxy, tert-butoxy and the like. The teens "alkenyl" and "alkynyl" refer to unsaturated aliphatic groups analogous to alkyls, but which contain at least one double or triple bond respectively. Suitable alkenyl and alkynyl groups include groups having 2 to about 12 carbon atoms, or from 1 to about 6 carbon atoms.

The term "alicyclic group" includes closed ring structures of three or more carbon atoms. Alicyclic groups include cycloparaffins or naphthenes which are saturated cyclic hydrocarbons, cycloolefins, which are unsaturated with two or more double bonds, and cycloacetylenes which have a triple bond. They do not include aromatic groups. Examples of cycloparaffins include cyclopropane, cyclohexane and cyclopentane. Examples of cycloolefins include cyclopentadiene and cyclooctatetraene. Alicyclic groups also include fused ring structures and substituted alicyclic groups such as alkyl substituted alicyclic groups. In the instance of the alicyclics such substituents can further comprise a lower alkyl, a lower alkenyl, a lower alkoxy, a lower alkylthio, a lower alkylamino, a lower alkylcarboxyl, a nitro, a hydroxyl, —$CF_3$, —CN, or the like.

The term "heterocyclic group" includes closed ring structures in which one or more of the atoms in the ring is an element other than carbon, for example, nitrogen, sulfur, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxy, —$CF_3$, —CN, or the like. Suitable heteroaromatic and heteroalicyclic groups generally will have 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

The term "aromatic group" includes unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

The term "alkyl" includes saturated aliphatic groups, including straight-chain alkyl groups, branched-chain alkyl groups, cycloalkyl (alicyclic) groups, alkyl substituted cycloalkyl groups and cycloalkyl substituted alkyl groups. In certain embodiments, a straight chain or branched chain alkyl has 30 or fewer carbon atoms in its backbone, e.g., $C_1$-$C_{30}$ for straight chain or $C_3$-$C_{30}$ for branched chain. In certain embodiments, a straight chain or branched chain alkyl has 20 or fewer carbon atoms in its backbone, e.g., $C_1$-$C_{20}$ for straight chain or $C_3$-$C_{20}$ for branched chain, and in some embodiments 18 or fewer Likewise, particular cycloalkyls have from 4-10 carbon atoms in their ring structure and in some embodiments have 4-7 carbon atoms in the ring structure. The term "lower alkyl" refers to alkyl groups having from 1 to 6 carbons in the chain and to cycloalkyls having from 3 to 6 carbons in the ring structure.

Moreover, the term "alkyl" (including "lower alkyl") as used throughout the specification and claims includes both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl, e.g., having 1 to 3 separate or fused rings and from 6 to about 18 carbon ring atoms, e.g., phenylmethyl (benzyl).

The term "aryl" includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine and the like. Aryl groups also include polycyclic fused aromatic groups such as naphthyl, quinolyl, indolyl and the like. The aromatic ring can be substituted at one or more ring positions with such substituents, e.g., as described above for alkyl groups. Suitable aryl groups include unsubstituted and substituted phenyl groups. The term "aryloxy" as used herein means an aryl group, as defined above, having an oxygen atom attached thereto.

The term "aralkoxy" as used herein means an aralkyl group, as defined above, having an oxygen atom attached thereto. Suitable aralkoxy groups have 1 to 3 separate or fused rings and from 6 to about 18 carbon ring atoms, e.g., O-benzyl.

The term "amino," as used herein, refers to an unsubstituted or substituted moiety of the formula —NR$_a$R$_b$, in which R$_a$ and R$_b$ are each independently hydrogen, alkyl, aryl, or heterocyclyl, or R$_a$ and R$_b$, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. An "amino-substituted amino group" refers to an amino group in which at least one of R$_a$ and R$_b$, is further substituted with an amino group.

The term "protecting group," as used herein, refers to chemical modification of functional groups that are well known in the field of organic synthesis. Exemplary protecting groups can vary, and are generally described in *Protective Groups in Organic Synthesis* [T. W. Green and P. G. M. Wuts, John Wiley & Sons, Inc, 1999].

"Hybrid," including "organic-inorganic hybrid material," includes inorganic-based structures wherein an organic functionality is integral to both the internal or "skeletal" inorganic structure as well as the hybrid material surface. The inorganic portion of the hybrid material may be, e.g., alumina, silica, titanium, cerium, or zirconium or oxides thereof, or ceramic material. As noted above, exemplary hybrid materials are shown in U.S. Pat. Nos. 4,017,528, 6,528,167, 6,686,035, 7,175,913 and 7,919,177, the disclosures of which are hereby incorporated in their entirety.

The term "BEH," as used herein, refers to an organic-inorganic hybrid material which is an ethylene bridged hybrid material.

The term "adsorbed group," as used herein, represents a monomer, oligimer or polymer, crosslinked or non-crosslinked that is non-covalently attached to the core material. In certain embodiments, wherein Z represents an adsorbed group, the group can be adsorbed onto the core material, X, the surface of the core material, X, or the surface of the stationary phase material. Examples include, but are not limited to alcohols, amines, thiols, polyamines, dedrimers, or polymers.

The term "functionalizing group" or "functionalizable group" includes organic functional groups which impart a certain chromatographic functionality to a stationary phase.

The term "terminal group," as used herein, represents a group which cannot undergo further reactions. In certain embodiments, a terminal group may be a hydrophilic terminal group. Hydrophilic terminal groups include, but are not limited to, protected or deprotected forms of an alcohol, diol, glycidyl ether, epoxy, triol, polyol, pentaerythritol, pentaerythritol ethoxylate, 1,3-dioxane-5,5-dimethanol, tris (hydroxymethyl)aminomethane, tris(hydroxymethyl)aminomethane polyglycol ether, ethylene glycol, propylene glycol, poly(ethylene glycol), poly(propylene glycol), a monovalent, divalent, or polyvalent carbohydrate group, a multiantennary carbohydrate, a dendrimer containing peripheral hydrophilic groups, a dendrigraph containing peripheral hydrophilic groups, or a zwitterion group.

The term "surface attachment group," as used herein, represents a group which may be reacted to covalently bond, non-covalently bond, adsorb, or otherwise attach to the core material, the surface of the core material, or the surface of the stationary phase material. In certain embodiments, the surface attachment group is attached to the surface of the core material by a siloxane bond. Surface attachment groups can provide covalent linkage between a solid stationary phase and an enzyme.

Solid Stationary Phases

IMER apparatuses, methods, and kits according to the technology can employ various solid stationary phases, linkers, and enzymes to achieve high-pressure, continuous flow operation and analysis of liquid samples comprising a polymer analyte. One example is BEH (e.g., Waters Corporation, Massachusetts, USA, BEH 130 Angstrom, BEH 200 Angstrom, or BEH 300 Angstrom). Pressure can mean actual chamber pressure (e.g., as opposed to pressure per mm of solid stationary phase bed).

In general, the solid stationary phase can include essentially any material selected and/or adaptable for high pressure IMER operation and covalent linkage to an enzyme. High pressure can include, for example, a pressure above about 2,000, 2,250, 2,500, 2,750, 3,000, 3,250, 3,500, 3,750, 4,000, 4,250, 4,500, 4,750, 5,000, 5,250, 5,500, 5,750, or 6,000 psi or a pressure up to about 5,000, 6,000, 7,000, 8,000, 9,000 10,000, 11,000, 12,000, 13,000, 14,000, 15,000, 16,000, 17,000, 18,000, 19,000, 20,000, 22,500, 25,000, 27,500, 30,000, 32,500, or 35,000 psi or any individual value or range therebetween. Higher pressures are also contemplated by the technology. For example, pressures up to about 40,000, 45,000, 50,000, 75,000, 100,000, 125,000, 150,000 or greater. In general, pressure should be selected in view of the solid support, instrument system, and desired flow rate. Covalent linkage to an enzyme may be achieved through a functional group on the surface of the solid stationary phase or through a linker molecule.

In various embodiments, the solid stationary phase can include inorganic/organic hybrid particles. One example inorganic/organic hybrid is ethylene-bridged (BEH) particles (Waters Corporation, Massachusetts, USA). The solid stationary phase can include a monolith, particles, porous particles, and/or superficially porous particles. Particles can be spherical or non-spherical. The solid stationary phase can include silica, inorganic silica, and/or metal oxide. In some embodiments, the chamber is equipped with one or more frits to contain the stationary phase material. In embodiments in which the stationary phase material is monolithic, the housing may be used without the inclusion of one or more frits.

The solid stationary phase can include, for example, particles having a mean size within the range of 1-10 microns, though a smaller or larger size could be selected if appropriate for a desired application. In various examples, the mean particle size is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.4, 3.5, 3.6, 3.7, 3.8, 3.9, 4.0, 4.5, 5.0, 5.5, 6.0, 6.5, 7.0, 7.5, 8, 8.6, 9, 9.5, or 10 microns. In general, particle size can be selected in view of the desired pressure and/or flow rate. For example, larger particle size can be used to achieve consistent pressure from a column head to an end during high pressurized digestion. The solid stationary phase can include pores having a mean pore volume within the range of 0.1-2.5 cm$^3$/g. In various examples, the mean pore volume is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 cm$^3$/g. In some embodiments, porous particles may be advantageous because they provide a relatively large surface area (per unit mass or column volume) for protein coverage at the same time as the ability to withstand high pressure.

The solid stationary phase can include pores having a mean pore diameter within the range of 100-1000 Angstroms. For example, the mean pore diameter can be about 100, 200, 300, 400, 500, 600, 700, 800, 900, 1000, or any value or range therebetween.

In certain embodiments, said stationary phase material comprises particles or a monolith having a core composition and a surface composition represented by Formula 1:

W—[X]-Q         Formula 1 where X is core composition having a surface comprising a silica core material, a metal oxide core material, an organic-inorganic hybrid core material or a group of block polymers thereof; W is hydrogen or hydroxyl; and Q is absent or is a functional group that minimizes electrostatic interactions, Van der Waals interactions, Hydrogen-bonding interactions or other interactions with an analyte.

Furthermore, in certain embodiments, W and Q occupy free valences of the core composition, X, or the surface of the core composition. In some embodiments, W and Q are selected to form a surface composition. In other embodiments, X may be selected to form a block polymer or group of block polymers.

In certain embodiments, X is silica, titanium oxide, aluminum oxide or an organic-inorganic hybrid core comprising an aliphatic bridged silane. In specific embodiments, X is an organic-inorganic hybrid core comprising a aliphatic bridged silane. In certain other specific embodiments, the aliphatic group of the aliphatic bridged silane is ethylene.

In certain embodiments, the core material, X, may be cerium oxide, zirconium oxides, or a ceramic material. In certain other embodiments, the core material, X, may have a chromatographically enhancing pore geometry (CEPG). CEPG includes the geometry, which has been found to enhance the chromatographic separation ability of the material, e.g., as distinguished from other chromatographic media in the art. For example, a geometry can be formed, selected or constructed, and various properties and/or factors can be used to determine whether the chromatographic separations ability of the material has been "enhanced," e.g., as compared to a geometry known or conventionally used in the art. Examples of these factors include high separation efficiency, longer column life and high mass transfer properties (as evidenced by, e.g., reduced band spreading and good peak shape). These properties can be measured or observed using art-recognized techniques. For example, the chromatographically-enhancing pore geometry of the present porous inorganic/organic hybrid particles is distinguished from the prior art particles by the absence of "ink bottle" or "shell shaped" pore geometry or morphology, both of which are undesirable because they, e.g., reduce mass transfer rates, leading to lower efficiencies. Chromatographically-enhancing pore geometry is found in hybrid materials containing only a small population of micropores. A small population of micropores is achieved in hybrid materials when all pores of a diameter of about <34 angstroms contribute less than about 110 m²/g to the specific surface area of the material. Hybrid materials with such a low micropore surface area (MSA) give chromatographic enhancements including high separation efficiency and good mass transfer properties (as evidenced by, e.g., reduced band spreading and good peak shape). Micropore surface area (MSA) is defined as the surface area in pores with diameters less than or equal to 34 angstroms, determined by multipoint nitrogen sorption analysis from the adsorption leg of the isotherm using the Barrett-Joyner-Halenda (BJH) method.

As used herein, the acronyms "MSA" and "MPA" are used interchangeably to denote "micro pore surface area."

In certain embodiments the core material, X, may be surface modified with a surface modifier having the formula $Z'_a(R')_b Si—R''$, where $Z'$=Cl, Br, I, $C_1$-$C_5$ alkoxy, dialkylamino or trifluoromethanesulfonate; a and b are each an integer from 0 to 3 provided that a+b=3; R' is a $C_1$-$C_6$ straight, cyclic or branched alkyl group, and R'' is a functionalizing group. In another embodiment, the core material, X, may be surface modified by coating with a polymer.

In certain embodiments, the surface modifier is selected from the group consisting of octyltrichlorosilane, octadecyltrichlorosilane, octyldimethylchlorosilane and octadecyldimethylchlorosilane. In some embodiments, the surface modifier is selected from the group consisting of octyltrichlorosilane and octadecyltrichlorosilane. In other embodiments, the surface modifier is selected from the group consisting of an isocyanate or 1,1'-carbonyldiimidazole (particularly when the hybrid group contains a $(CH_2)_3OH$ group).

In another embodiment, the material has been surface modified by a combination of organic group and silanol group modification. In still another embodiment, the material has been surface modified by a combination of organic group modification and coating with a polymer. In a further embodiment, the organic group comprises a chiral moiety. In yet another embodiment, the material has been surface modified by a combination of silanol group modification and coating with a polymer.

In other embodiments, the material has been surface modified via formation of an organic covalent bond between an organic group on the material and the modifying reagent. In still other embodiments, the material has been surface modified by a combination of organic group modification, silanol group modification and coating with a polymer. In another embodiment, the material has been surface modified by silanol group modification. In certain embodiments, the surface modified layer may be porous or nonporous.

In other embodiments of the stationary phase material, Q is a hydrophilic group, a hydrophobic group or absent. In some embodiments of the stationary phase material, wherein Q is a hydrophilic group, Q is an aliphatic group. In other embodiments, said aliphatic group is an aliphatic diol. In still other embodiments, Q is represented by Formula 2:

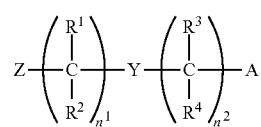         Formula 2 wherein $n^1$ an integer from 0-30; $n^2$ an integer from 0-30; each occurrence of $R^1$, $R^2$, $R^3$ and $R^4$ independently represents hydrogen, fluoro, lower alkyl, a protected or deprotected alcohol, a zwiterion, or a group Z; Z represents:
a) a surface attachment group produced by formation of covalent or non-covalent bond between the surface of the stationary phase material with a moiety of Formula 3:

$(B^1)_x(R^5)_y(R^6)_z Si—$         Formula 3 wherein x is an integer from 1-3,
y is an integer from 0-2,
z is an integer from 0-2,
and x+y+z=3 each occurrence of $R^5$ and $R^6$ independently represents methyl, ethyl, n-butyl, iso-butyl, tert-butyl, iso-propyl, thexyl, substituted or unsubstituted aryl, cyclic alkyl, branched alkyl, lower alkyl, a protected or deprotected alcohol, or a zwiterion group;

$B^1$ represents —$OR^7$, —$NR^{7'}R^{7''}$, —$OSO_2CF_3$, or —Cl; where each of $R^{7'}$ $R^{7'}$ and $R^{7'''}$ represents hydrogen, methyl, ethyl, n-butyl, iso-butyl, tent-butyl, iso-propyl, thexyl, phenyl, branched alkyl or lower alkyl;

b) a direct attachment to a surface hybrid group of X through a direct carbon-carbon bond formation or through a heteroatom, ester, ether, thioether, amine, amide, imide, urea, carbonate, carbamate, heterocycle, triazole, or urethane linkage; or c) an adsorbed group that is not covalently attached to the surface of the stationary phase material;

d) a surface attachment group produced by formation of a covalent bond between the surface of the stationary phase material, when W is hydrogen, by reaction with a vinyl or alkynyl group;

Y represents a direct bond; a heteroatom linkage; an ester linkage; an ether linkage; a thioether linkage; an amine linkage; an amide linkage; an imide linkage; a urea linkage; a thiourea linkage; a carbonate linkage; a carbamate linkage; a heterocycle linkage; a triazole linkage; a urethane linkage; a diol linkage; a polyol linkage; an oligomer of styrene, ethylene glycol, or propylene glycol; a polymer of styrene, ethylene glycol, or propylene glycol; a carbohydrate group, a multi-antennary carbohydrates, a dendrimer or dendrigraphs, or a zwitterion group; and A represents
i.) a hydrophilic terminal group;
ii.) hydrogen, fluoro, fluoroalkyl, lower alkyl, or group Z; or
iii.) a functionalizable group.

In certain embodiments, wherein Q is an aliphatic diol of Formula 2, $n^1$ an integer from 2-18, or from 2-6. In other embodiments, wherein Q is an aliphatic diol of Formula 2, $n^2$ an integer from 0-18 or from 0-6. In still other embodiments, wherein Q is an aliphatic diol of Formula 2, $n^1$ an integer from 2-18 and $n^2$ an integer from 0-18, $n^1$ an integer from 2-6 and wherein $n^2$ an integer from 0-18, $n^1$ an integer from 2-18 and $n^2$ an integer from 0-6, or $n^1$ an integer from 2-6 and $n^2$ an integer from 0-6

In yet other embodiments of the stationary phase material, wherein Q is an aliphatic diol of Formula 2, A represents i) a hydrophilic terminal group and said hydrophilic terminal group is a protected or deprotected forms of an alcohol, diol, glycidyl ether, epoxy, triol, polyol, pentaerythritol, pentaerythritol ethoxylate, 1,3-dioxane-5,5-dimethanol, tris(hydroxymethyl)aminomethane, tris(hydroxymethyl)aminomethane polyglycol ether, ethylene glycol, propylene glycol, poly(ethylene glycol), poly(propylene glycol), a mono-valent, divalent, or polyvalent carbohydrate group, a multi-antennary carbohydrate, a dendrimer containing peripheral hydrophilic groups, a dendrigraph containing peripheral hydrophilic groups, or a zwitterion group.

In still other embodiments of the stationary phase material, wherein Q is an aliphatic diol of Formula 2, A represents ii.) hydrogen, fluoro, methyl, ethyl, n-butyl, t-butyl, i-propyl, lower alkyl, or group Z.

In still yet other embodiments of the stationary phase material, wherein Q is an aliphatic diol of Formula 2, A represents iii.) a functionalizable group, and said functionalizable group is a protected or deprotected form of an amine, alcohol, silane, alkene, thiol, azide, or alkyne. In some embodiments, said functionalizable group can give rise to a new surface group in a subsequent reaction step wherein said reaction step is coupling, metathesis, radical addition, hydrosilylation, condensation, click, or polymerization.

In still other embodiments, the group Q can be a surface modifier. Non-limiting examples of surface modifiers that can be employed for these materials include:

A.) Silanes that result in a hydrophollic surface modification

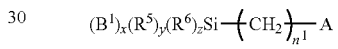

| | Hydrophillic Surface | | | | |
|---|---|---|---|---|---|
| Option | $B^1$ | $R^5$ | $R^6$ | x/y/z | $n^1$ |
| 1 | chloro, methoxy, or ethoxy | — | — | 3/0/0 | 3 |
| 2 | chloro, methoxy, or ethoxy | methyl, ethyl, n-propyl, i-propyl, or t-butyl | — | 2/1/0 | 3 |
| 3 | chloro, methoxy, or ethoxy | methyl, ethyl, n-propyl, i-propyl, or t-butyl | — | 1/2/0 | 3 |
| 4 | chloro, methoxy, or ethoxy | methyl, ethyl, n-propyl, i-propyl, or t-butyl | methyl, ethyl, n-propyl, i-propyl, or t-butyl | 1/1/1 | 3 |

Where A is selected from the following:

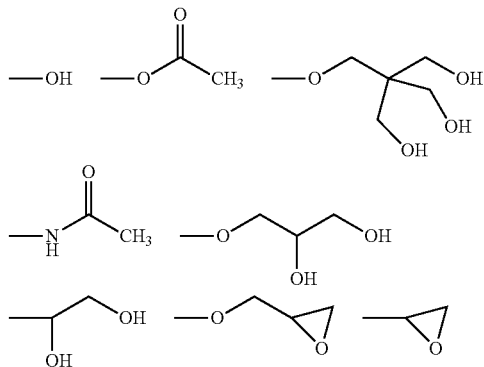

13

-continued

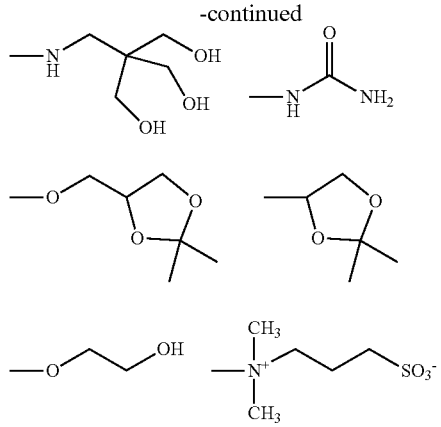

14

-continued

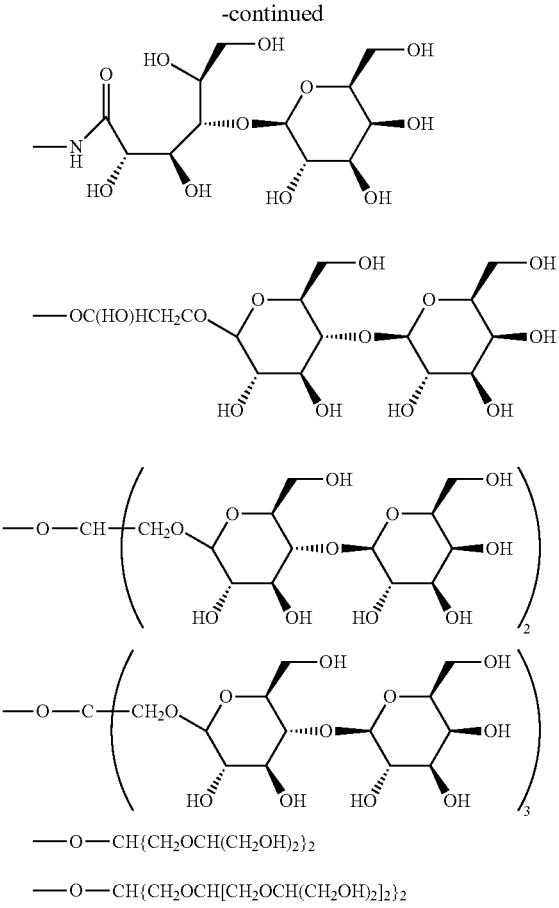

—O—CH{CH$_2$OCH(CH$_2$OH)$_2$}$_2$

—O—CH{CH$_2$OCH[CH$_2$OCH(CH$_2$OH)$_2$]$_2$}$_2$ or

B) silanes that result in a hydrophobic or a mixed hydrophollic/hydrophobic surface modification

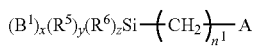

| | Hydrophobic Surface | | | | |
|---|---|---|---|---|---|
| Option | B$^1$ | R$^5$ | R$^6$ | x/y/z | n$^1$ |
| 1 | chloro, methoxy, or ethoxy | — | — | 3/0/0 | 1-18 |
| 2 | chloro, methoxy, or ethoxy | methyl, ethyl, n-propyl, i-propyl, or t-butyl | — | 2/1/0 | 3-18 |
| 3 | chloro, methoxy, or ethoxy | methyl, ethyl, n-propyl, i-propyl, or t-butyl | — | 1/2/0 | 1-3-18 |
| 4 | chloro, methoxy, or ethoxy | methyl, ethyl, n-propyl, i-propyl, or t-butyl | methyl, ethyl, n-propyl, i-propyl, or t-butyl | 1/1/1 | 3-18 |

Where A is selected from the following; H, phenyl, NHC(O)NHR$^8$, NHC(O)R$^8$, OC(O)NHR$^8$, OC(O)OR$^8$, or triazole-R$^8$, where R$^8$ is octadecyl, dodecyl, decyl, octyl, hexyl, n-butyl, t-butyl, n-propyl, i-propyl, phenyl, benzyl, phenethyl, phenylethyl, phenylpropyl, diphenylethyl, biphenylyl.

In certain embodiments, Z represents an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage.

In other embodiments, Z represents an adsorbed, surface group that is not covalently attached to the surface of the material. This surface group can be a cross-linked polymer, or other adsorbed surface group. Examples include, but are not limited to alcohols, amines, thiols, polyamines, dedrimers, or polymers.

Enzymes

IMER apparatuses, methods, and kits according to the technology can employ various enzymes to achieve high-pressure, continuous flow operation and analysis of liquid samples comprising a polymer analyte. One example is pepsin, which is employed in HDX MS for sample preparation.

In general, the enzyme can include essentially any protein catalyst that can function for sample preparation or analysis. One example enzyme is a protease. A protease can be a specific cleavage protease (e.g., trypsin) or a non-specific cleavage protease (e.g., pepsin). The technology can be used with numerous different types of enzyme such as trypsin, chymotrypsin, lysC, amidases, PNGase, PNGase F, V8, as well as mixtures of these and/or other enzymes, in various proteomics applications. A protease can be selected from any one of the following broad groups: Serine proteases, Threonine proteases, Cysteine proteases, Aspartate proteases, Metalloproteases, and Glutamic acid proteases. Alternatively, protease can be selected from any one of the following broad groups: Acid proteases, Neutral proteases, or Basic proteases (or alkaline proteases). The enzyme can include a combination of more than one protease (e.g., having cumulative and/or complementary functions). The enzyme (or enzymes) can be selected to achieve a desired function (e.g., cleaving one or more specific bonds) and/or operate under desired conditions (e.g., matching an enzyme's operating pH to the pH of a sample).

In addition to the enzyme, the solid stationary phase can be linked to a capture group. The capture group can be a high affinity/specific capture agent (e.g., an antibody or antibody conjugate) or a low affinity/nonspecific capture agent. The capture group can be covalently linked to the solid stationary phase. The capture group can provide a second mode of action (e.g., increase the resonance time of the polymer analyte, thereby increasing the efficiency of the IMER).

Covalent Linkers

IMER apparatuses, methods, and kits according to the technology can employ various linkers to immobilize an enzyme of interest on a solid stationary phases. One example is Triethoxysilylbutyraldehyde (bALD-TEOS, available from Gelest, Inc.)

In general, the covalent linker can include essentially any chemical moiety that can covalently connect the solid stationary phase and the enzyme (e.g., an amide bond formed by a carboxylic acid and an amine). Other examples included amines and NHS-aldehydes such as succinimidyl p-formylbenzoate (SFB) or succinimidyl p-formylphenoxyacetate (SFPA), as well as amines and glutaraldehydes. In certain embodiments, the covalent linker can include an organofunctionalized silane linker. The organofunctionalized silane linker can be triethoxysilylbutyraldehyde. In general, enzymes can be covalently joined to a linker through Schiff base formation and reductive amination. In general, silane linkers can be covalently joined to a solid support having hydroxyl groups through contacting the linker and solid support, and quenching the reaction mixture with ethanolamine. Other enzymes can be immobilized on a solid support such as BEH using an appropriate immobilization protocol (e.g., selected for the chemical functionality of the solid support and binding site on the protein). Depending on the enzymatic activity at a targeted pH, a different pH may be required during immobilization protocol. For example, a BEH trypsin column may need to be prepared at a neutral pH rather than an acidic pH.

FIG. 1 shows an example solid stationary phase preparation reaction. First, an enzyme (pepsin) is reacted with a linker (Triethoxysilylbutyraldehyde, bALD-TEOS) through Schiff base formation and reductive amination by NaCNBH$_3$. Second, enzyme-linker is reacted with alcohol groups on the surface of the solid support (acid treated BEH) and quenched with ethanolamine.

bALD-TEOS is an aldehyde compound that forms Schiff Base with a primary or secondary amine (NH—). Every protein contains the N-terminus with a free amine, thus the N-terminus of a pepsin and any available side-chain amine groups are subjected to form a Schiff Base conjugate with bALD-TEOS.

The ALD coupling solution (Sterogene Bioseparation, Inc.) was added into the conjugate mixture as a mild reductant (NaCNBH$_3$) to initiate the reductive amination. Once the Schiff base is reduced through an agitated incubation for 2 hours, this type of linkage becomes stable.

Acid treated BEH (5 micron diameter, 300 Angstrom pore size) was added into the solution containing the reduced conjugate of bALD-TEOS and pepsin. The other end of bALD-TEOS contains the triethoxysily groups available to react with hydroxyl group of silanol on the surface of BEH particles. The reaction was completed after overnight rotation, and then quenched by adding 1M ethanolamine to block the unreacted aldehyde groups.

The batches of pepsin BEH were washed with Na$_3$Citrate, NaCl, and finally washed and stored in 0.08% TFA in water. Pepsin is irreversibly deactivated under basic conditions. Thus the pH of the pepsin solution was kept acidic under pH 5 throughout the batch synthesis.

The solid stationary phase linked to the enzyme can then be placed in a chamber (e.g., a column such as the 2.1×30 mm UPLC housing with 0.1% formic acid in water) for use in an IMER system. In various embodiments, the chamber can be an UPLC housing. However, in general, the chamber need only be adapted for online, high pressure operation and may assume a variety of geometric configurations (e.g., short and squat for lower resonance times or long and thin for longer resonance times).

High Pressure Systems

IMERs can be used under high pressure, for example, in high pressure LC systems. One example is the nanoACQUITY UltraPerformance LC® (UPLC®) system available from Waters Corporation (Massachusetts, USA) combined with Waters Corporation SYNAPT™ Q-TOF™ mass spectrometry and acquired in elevated-energy mass spectrometry (MSE) mode and processed using a Waters Corporation ProteinLynx Global SERVER™ (PLGS, which is a fully integrated Mass-Informatics™ platform for quantitative and qualitative proteomics research).

Figure 2A:
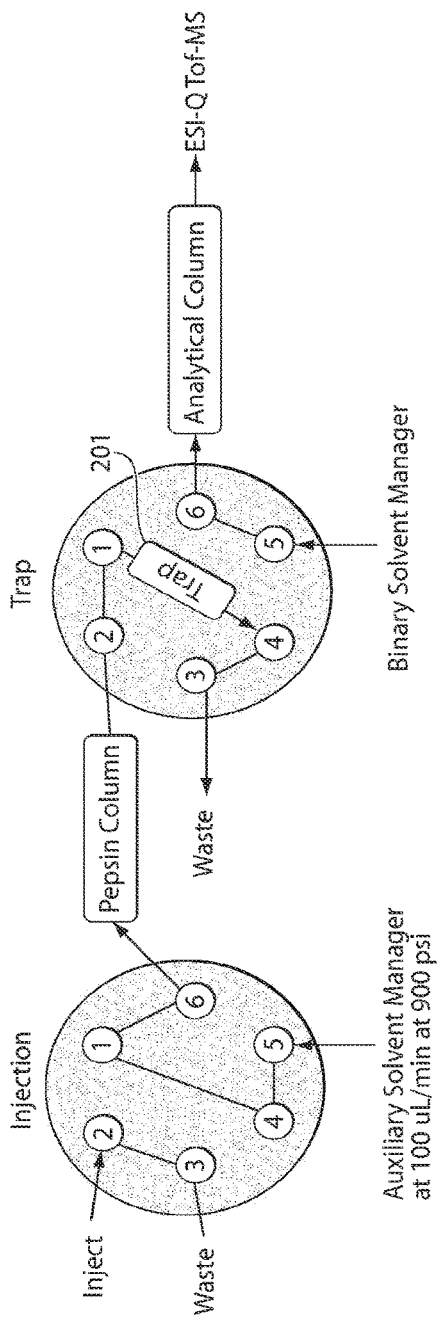
FIGS. 2A-C each shows a schematic of an example IMER system.
Figure 2B:
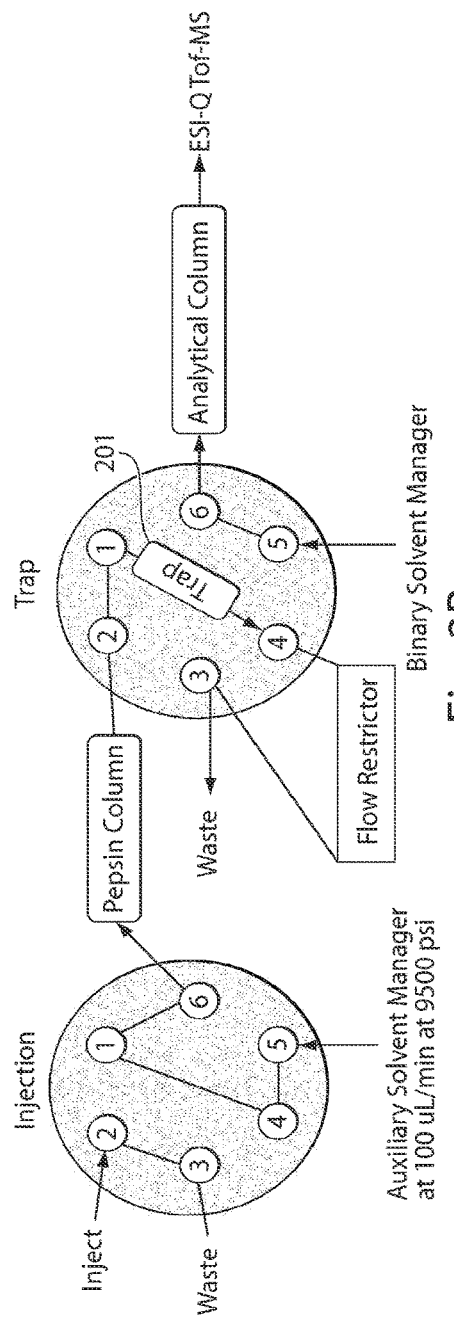
Figure 2C:
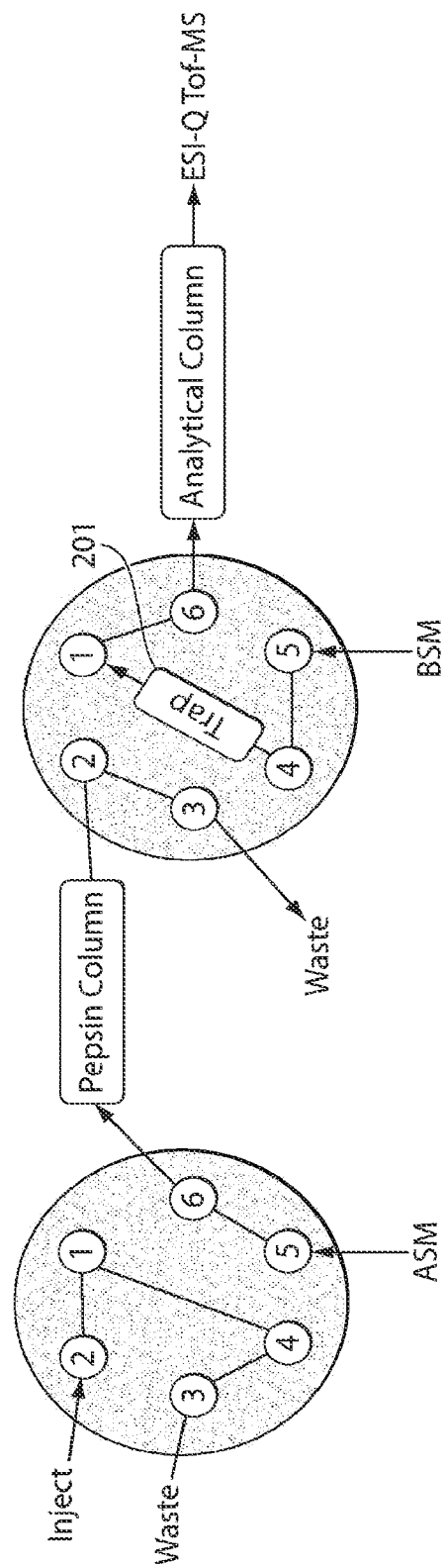

FIGS. 2A-C show schematics of exemplary on-line IMER systems. A pepsin column was prepared by the method shown in FIG. 1, using pepsin, bALD-TEOS, and BEH 5 micron, 300 Angstrom particles. The pepsin-BEH particles were packed in UPLC column hardware (2.1×30 mm), which was then installed on a nanoACQUITY UltraPerformance LC®. The IMER system was set up and operated on-line for HDX-MS, which increased the speed and convenience of the analysis.

The IMER system components included two 6-port valves (i.e., each port labeled 1-6 in the schematics shown in FIGS. 2A-C), which are shown in the positions corresponding to the stage of experiments. 100 µL/min of 0.05% formic acid pH 2.5 was flowed in auxiliary solvent manager through pepsin column. The gradient at 40 µL/min was flowed in a binary solvent manager. In each case, the protein sample was loaded into pepsin column and digested for approximately 30 seconds. FIGS. 2A and 2B show the system operating with the valve in trapping mode. FIG. 2A shows the experimental setup for a low pressure (900 psi) and FIG. 2B shows the experimental setup for a high pressure (9,500 psi). In the experiment shown in FIG. 2B, a 2.1×150 mm column was placed after a trapping column, to function as a flow restrictor (e.g., a pressure modulator).

Although the example flow restrictor (e.g., pressure modulator) is shown a 2.1×150 mm column was placed after a trapping column, flow resistors can be essentially any structure or device that creates and/or maintains pressure in the system. For example, a flow resistor can be a capillary tubing, packed column, or microfluidic device.

A Waters Corporation (Massachusetts, USA) trapping column 201 (2.1×5 mm BEH C18, 1.7 micron diameter) was used to remove salts from the digested peptides in a desalting step. After the digestion and consequent trapping (3 minutes), the valves were switched from trapping mode to eluting mode, and the peptides were separated in an analytical column for MS analysis.

FIG. 2C shows the IMER system with the valve in eluting mode. Trapped peptides were released from trap column and separated in analytical column using a solvent gradient. During eluting mode, high pressure was not applied to the pepsin column. The solvent flow went through the pepsin column directed into waste. The binary solvent manager (BSM) drove the flow to the trapping column to elute the trapped peptides. Finally the peptides were separated in analytical column.

In another set of experiments, a trypsin column was used in place of the pepsin column in the inline IMER system shown in FIGS. 2A-C. With the trypsin column, the auxiliary solvent manager (ASM) delivered 20 mM ammonium bicarbonate at pH 7.9 with flow rate at 10 µL/min.

The apparatus and methods described in connection with FIGS. 2A-C were used to digest multiple model proteins including phosphorylase b, bovine serum albumin, cytochrome C, and a monoclonal antibody. In each case, the online, high pressure IMER exhibited high digestion efficiency and experimental reproducibility, as well as sequence coverage of up to 95% without deterioration of the solid stationary phase.

HDX MS is one example analytical technique for which the IMER system can be used. In another example, tryptic IMER can be used as an online tryptic digestion device (e.g., as an alternative to widely used offline tryptic digestion methods), which has various proteomics applications. In yet another example, the technology can be used for 2D LC online digestion for protein identification and/or characterization. In addition to sample preparation methods, the technology can be used with various analytical methods including refractive index detectors, UV detectors, light-scattering detectors and mass spectrometers.

Experimental Results

Figure 3A:
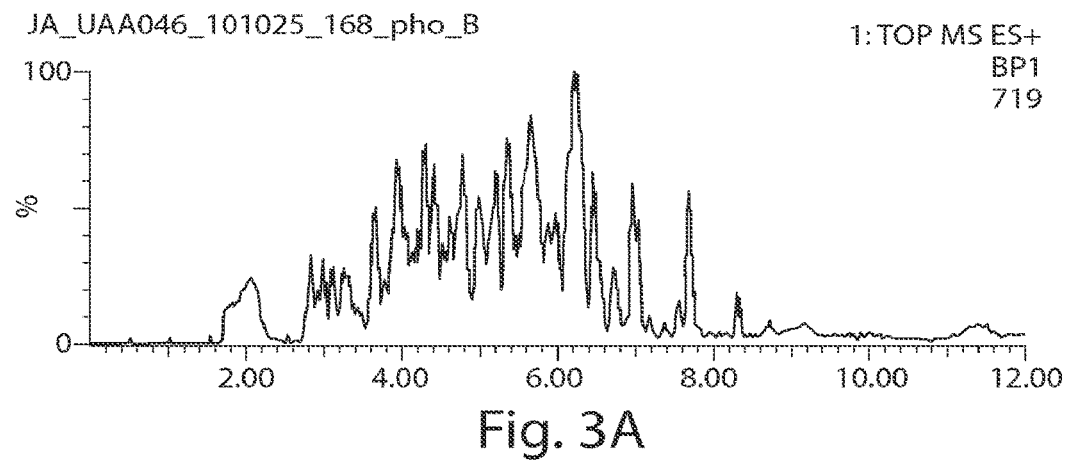
FIG. 3 shows a comparison of a 900 psi protein digestion (FIG. 3A) and a 9,500 psi protein digestion (FIG. 3B).
Figure 3B:
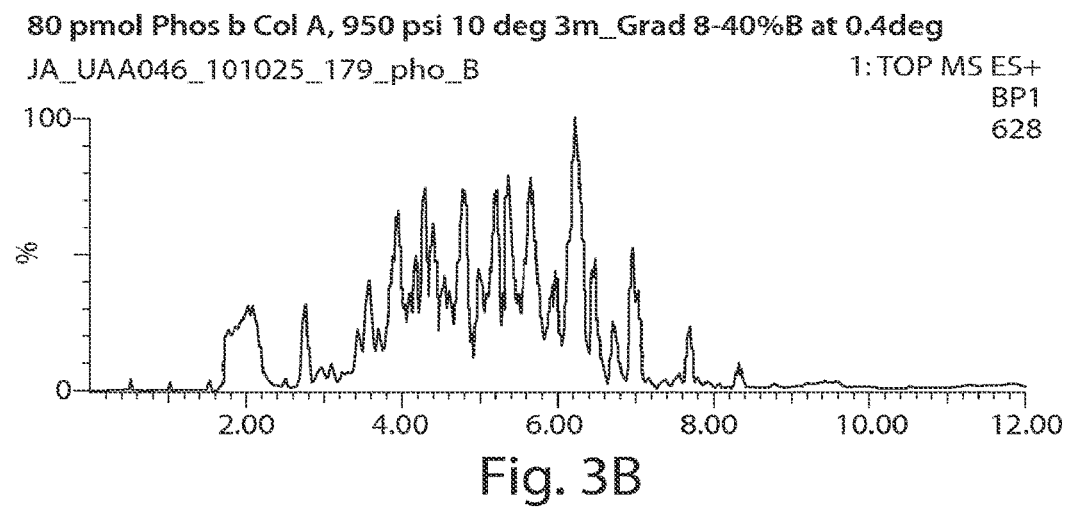

FIG. 3A shows a chromatogram of phosphorylase b after the 900 psi pepsin digestion described in connection with FIG. 2A. At 900 psi, phosphorylase b was digested to produce only 76% sequence coverage with 118 common peptides. In contrast, FIG. 3B shows a chromatogram of phosphorylase b after the 9,500 psi pepsin digestion described in connection with FIG. 2B. At 9,500 psi, phosphorylase b was digested to produce 82% sequence coverage with 139 common peptides, without any intact protein remaining. Therefore, the higher pressure digestion resulted in a greater number of peptides and a higher sequence coverage.

Figure 4:
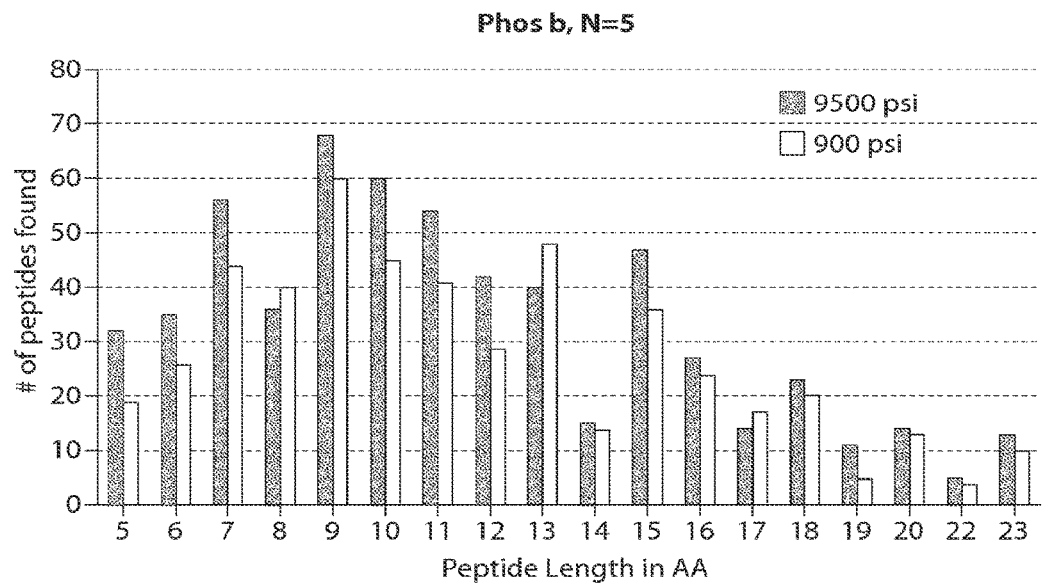
FIG. 4 shows a comparison of the number of peptide fragments produced from phosphorylase b under 900 psi and 9500 psi.

FIG. 4 shows a plot of the number of pepties for each peptide length of 4-23, for the 900 psi digestions (light bar on the right hand side, corresponding to FIGS. 2A and 3A) and for the 9,500 psi digestion (dark bar on the left hand side, corresponding to FIGS. 2B and 3B). Again, this figure illustrates that a high pressure lead to a greater number of shorter peptides (e.g., higher sequence coverage) in the digestion of phosphorylase b.

In general, pressurized digestion is also advantageous because it can increase digestion efficiency for proteins, including proteins that are difficult to digest at low pressure. Furthermore, the improved sequence coverage and digestion efficiency which results from the high-pressure, online apparatus and method of the technology is advantageous in proteomics applications such as HDX MS because it can provide improved resolution of localized conformational changes in higher order protein structure.

During the HDX MS, a phenomena called "back-exchange" can occur: once the hydrogen from protein backbone is exchanged with deuterium, the labeled deuterium can quickly go back to hydrogen when the temperature, pH, and pepsin column media are not properly controlled. Back-exchange causes a loss of information on localized conformational changes in higher order protein structures. Thus, it is important to achieve lower level of back-exchange through fast digestion and/or rapid desalting (e.g., a less than 10 minute separation) in HDX MS.

Figure 5:
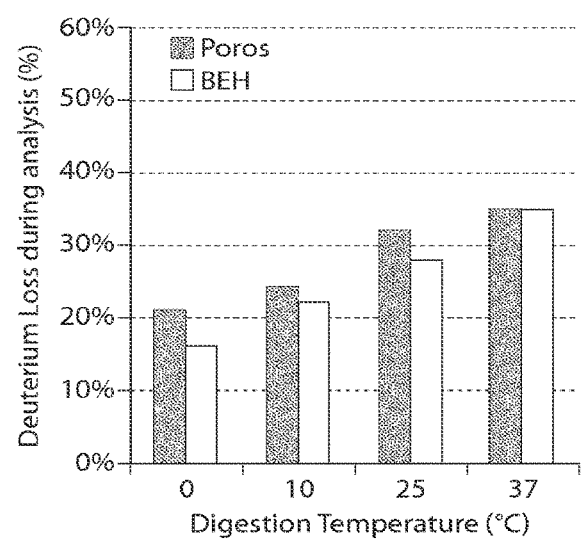
FIG. 5 shows a comparison of % back-exchange in a fully deuterated polypeptide in a POROS® column and a BEH column.

FIG. 5 shows % back-exchange at various temperatures in an HDX MS analysis of fully deuterated Bradykinin. The figure compares the % back-exchange in an embodiment of the present technology (an online, high pressure pepsin IMER setup described in FIG. 2B) and the % back-exchange from a low pressure POROS® pepsin column (a setup similar to FIG. 2A, commercially available from Applied Biosystems, California, USA). Both experiments in the comparison were performed with the same flow rate, temperature, and reagents. The only variable was the solid stationary phase and the pressure—the Poros apparatus was operated at low pressure and that apparatus according to an embodiment of the technology was operated online, at high pressure. At all temperatures below 37° C., the embodiment of the present technology exhibited a lower back-exchange rate than the POROS® column. Without intending to be bound by any particular theory, it is believed that the superior operation of the technology is due, at least in part, to the increased protein digestion efficiency at high pressure.

The foregoing illustrations and examples demonstrate the advantages of the technology in the context of HDX MS—increased protein digestion speed and efficiency, combined with reduced experimental artifacts and signal loss (e.g., back-exchange). These and other advantages in various proteomics and biotechnology application will be apparent to those of ordinary skill in the art.

While the technology has been particularly shown and described with reference to specific embodiments, it should be understood by those skilled in the art that various changes in form and detail may be made without departing from the spirit and scope of the technology as defined by the appended claims.

What is claimed is:

1. A method comprising:
    flowing a liquid sample comprising a polymer analyte over a solid stationary phase linked to an enzyme by a covalent linker in an online system under a pressure between about 2,500 and 35,000 psi, thereby cleaving the polymer analyte;
    wherein the solid stationary phase comprises particles having an organic-inorganic hybrid core comprising ethylene-bridged silanes wherein the ethylene bridged silanes are integral to both the internal inorganic structure and the surface of the organic-inorganic hybrid core, and wherein the particles have a mean pore volume within the range of 0.2 and 1.3 cm$^3$/g, a mean pore diameter within the range of 130 and 300 Angstroms and a mean particle size within the range of 1.5 and 10 microns.

2. The method of claim 1, wherein the covalent linker comprises triethoxysilylbutyraldehyde.

3. The method of claim 1, wherein the pressure is between about 8,000-15,000 psi.

4. The method of claim 1, further comprising:
    collecting analyte flowing out of the outlet;
    separating the collected analyte by liquid chromatography; and
    analyzing the separated analyte by mass spectrometry.

5. The method of claim 1, wherein the solid stationary phase is linked to a capture group.

6. The method of claim 1, wherein the enzyme comprises a protease.

7. The method of claim 1, wherein the enzyme comprises one or more of pepsin, trypsin, chymotrypsin, lysC, amidase, PNGase, PNGase F, or V8.

8. The method of claim 7, wherein the enzyme comprises trypsin or pepsin.

9. The method of claim 1, wherein the polymer analyte is a biopolymer analyte.

10. The method of claim 9, wherein the biopolymer analyte is a protein, a polypeptide, a carbohydrate, a deoxyribonucleic acid, or a ribonucleic acid.

11. The method of claim 10, wherein the biopolymer analyte is a protein.

12. The method of claim 1, wherein the covalent linker comprises an organo-functionlized silane linker.

* * * * *